(12) United States Patent
Bergstrand Borjegren et al.

(10) Patent No.: US 9,220,628 B2
(45) Date of Patent: Dec. 29, 2015

(54) NOSE PLUG

(75) Inventors: Susanna Bergstrand Borjegren, Sater (SE); Anders Proos, Sater (SE); Per Borjegren, Sater (SE)

(73) Assignee: NoseOption AB, Stockholm (SE)

( * ) Notice: Subject to any disclaimer, the term of this patent is extended or adjusted under 35 U.S.C. 154(b) by 290 days.

(21) Appl. No.: 13/703,511

(22) PCT Filed: Jun. 15, 2011

(86) PCT No.: PCT/SE2011/050742
§ 371 (c)(1),
(2), (4) Date: Dec. 11, 2012

(87) PCT Pub. No.: WO2011/162677
PCT Pub. Date: Dec. 29, 2011

(65) Prior Publication Data
US 2013/0081639 A1    Apr. 4, 2013

(30) Foreign Application Priority Data

Jun. 24, 2010    (SE) .................................... 1050698

(51) Int. Cl.
*A61F 9/00*    (2006.01)
*A61F 5/08*    (2006.01)
*A61M 15/08*    (2006.01)
*A62B 23/06*    (2006.01)

(52) U.S. Cl.
CPC .................. *A61F 5/08* (2013.01); *A61M 15/08* (2013.01); *A61M 2206/10* (2013.01); *A62B 23/06* (2013.01)

(58) Field of Classification Search
CPC ........................................................ A61F 5/08
USPC ......... 128/858, 857, 206.11, 207.18; 606/199
See application file for complete search history.

(56) References Cited

U.S. PATENT DOCUMENTS

| | | | |
|---|---|---|---|
| 4,221,217 A | 9/1980 | Amezcua | |
| 5,417,205 A | 5/1995 | Wang | |
| 5,787,884 A | 8/1998 | Tovey | |
| 7,207,333 B2 * | 4/2007 | Tohara | 128/206.11 |
| 2002/0096178 A1 * | 7/2002 | Ziaee | 128/207.18 |
| 2007/0106382 A1 | 5/2007 | Tohara | |
| 2009/0007919 A1 * | 1/2009 | Dolezal et al. | 128/206.11 |
| 2010/0331777 A1 * | 12/2010 | Danielsson | 604/104 |

FOREIGN PATENT DOCUMENTS

| | | |
|---|---|---|
| FR | 2417304 A1 | 9/1979 |
| FR | 2 631 229 A1 | 11/1989 |
| WO | 0162342 A1 | 8/2001 |
| WO | 2007/065083 A2 | 6/2007 |

OTHER PUBLICATIONS

Extended European Search Report, dated Jan. 28, 2014, from corresponding EP application.
International Search Report, dated Oct. 5, 2011, from corresponding PCT application.

* cited by examiner

*Primary Examiner* — Victoria J Hicks
(74) *Attorney, Agent, or Firm* — Young & Thompson

(57) ABSTRACT

A nose plug (1) includes at least one flexible member (2) and one rigid, elongated support member (3). The flexible member is arranged to surround the support member, and the flexible member is adapted to be placed within a nostril to accurately fill the opening of the nostril, and is provided with elements for enabling air flowing in a tortuous structure.

13 Claims, 4 Drawing Sheets

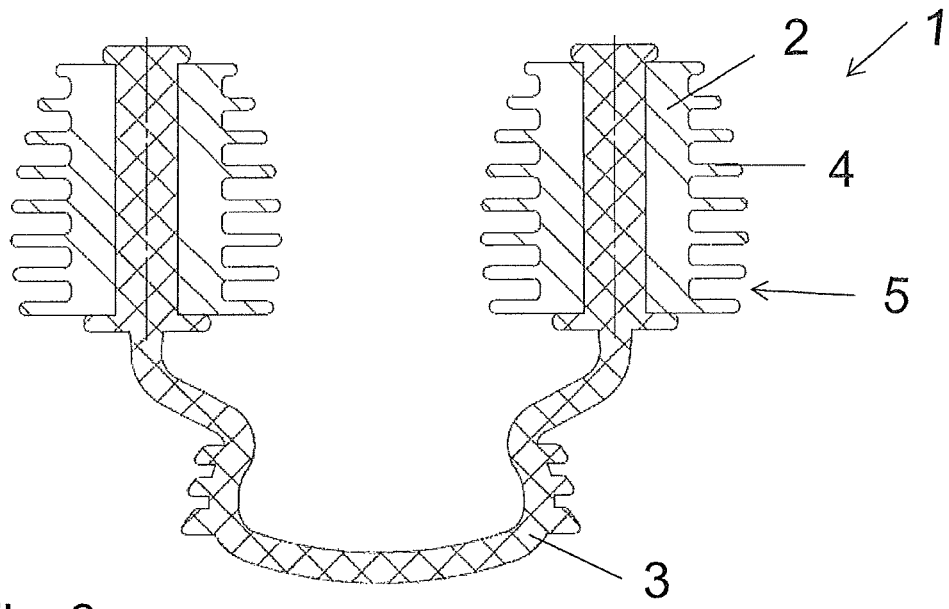
Fig. 3  A-A
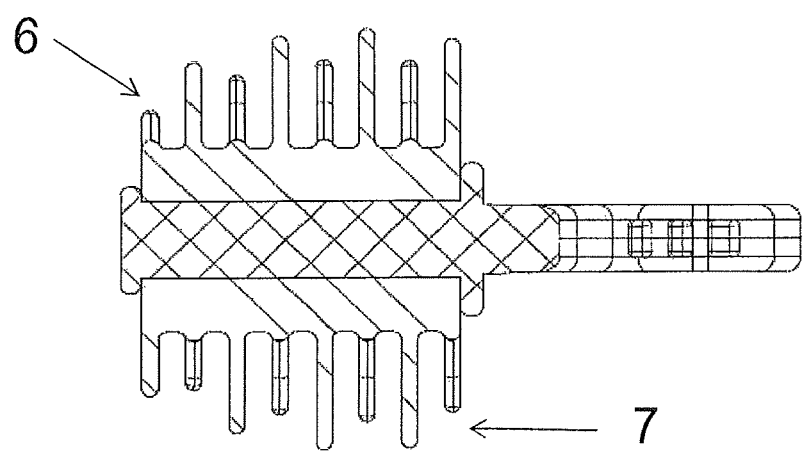
B-B
Fig. 4

NOSE PLUG

TECHNICAL FIELD

The invention relates to a nose plug comprising at least one flexible member and one rigid, elongated support member.

BACKGROUND

People working in the health care area are often exposed to bad odour. For instance people taking care of elderly people are working in surroundings were it may smell badly and thus, it is often desirable that work involving e.g. changing diapers is terminated as quickly as possible. When the work is done in great haste there is a risk that it is not performed correctly and the patient may also not be treated with dignity.

Other professions were it is necessary to be able to endure working in a surrounding where it might smell badly are rescue service staff, dentists, veterinary surgeons, people helping in emergency areas, medical service staff, etc. Certainly other people may also be exposed to bad odours and might feel uncomfortable because of this.

Traditionally people working in health care and other people working in an environment with a bad odour have been trying to endure in the environment, without any appliances that might hinder the stench to reach the olfactory organs. Alternatively, fragrance sprays or masks have been used.

Further, it is a problem that certain medicines are overdosed. When people catch a cold and the nose is stopped, they normally use a nasal spray in order to being able to properly breathe through the nose. It is a problem that nasal sprays often are used too much, too often or too long. This overdosing leads to reduced effect of the nasal spray.

Thus, it would be desirable to have access to some means for solving, among others, the above mentioned problems.

There is a need for a product that prevents bad odour to enter the nose and reach the olfactory organs. And there is also a need for product delivering medicines or other releasable substances with a long-term effect in a controlled manner through the nose. The product should be easy to breathe through, should be easy to handle and should not be offending the person being taken care of when the product is used, i.e. it should be a small and convenient product.

SUMMARY OF THE INVENTION

The object of the present invention is to address the problems outlined above. These objects, and others, are achieved by the apparatus according to the appended independent claim.

According to a first aspect, the invention provides a nose plug. The nose plug comprises at least one flexible member and one rigid, elongated support member. The flexible member is arranged to surround the support member, and the flexible member is adapted to be placed within a nostril to accurately fill the opening of the nostril. However, despite the plug filling the nostril, it is provided with means for guiding the flow of air entering the nostril in a serpentine or spiral like path by means of a plurality of plates or a band.

Thereby, air entering the nose is forced a longer distance than without the nose plug arranged in the nose.

In one embodiment the nose plug carries a releasable substance dispersed in the material of the flexible member or arranged on the surface of the flexible member. This is an advantage since the releasable substance may be taken up and delivered by the air, which is guided along an extended path.

In one embodiment of the invention the flexible member comprises a plurality of parallel plates arranged along the support member and where each plate extends in a direction perpendicular to the extension of the support member. There is provided for communication between the spaces formed by adjacent plates, such that the air is forced to pass between the plates whereby, the air is forced to flow an extended distance. The communication is preferably provided in that each plate has one recess at the periphery, and the recesses are arranged such that no recess overlaps a recess in a previous or subsequent plate. The flow of air is thus, being forced to pass through the openings created by the recesses and makes it easy to breathe through the nose plug.

In one embodiment the plates have a rounded shape, preferably elliptical. The plates may also have different sized peripheries. This is a preferred shape of the plates for the nose plug to properly adapt within a nostril.

In a preferred embodiment of the invention a first set of recesses are arranged on every second plate on a position at the periphery at one end of the transverse diameter and a second set of recesses are arranged on every plate there between at the periphery at the other end of the transverse diameter. The distance of the air flowing into the nose will be as long as possible, which is advantageously in order to efficiently deliver the releasable substance.

In one embodiment the flexible member comprises a helically arranged band forming a spiral like structure around the support member. This is an alternative way of designing the air flow path.

In one embodiment the flexible member and the support member are permanently fixed to each other. Thus, the flexible member will be an integrated part of the support member and will thus, not risk remaining inside the nose when the user pulls out the nose plug by means of the support member.

In another preferred embodiment the nose plug comprises two flexible members connected to each other by means of a generally U-shaped support member, each flexible member being attached at one leg of said U-shaped support member. The extension of the support member between the two flexible members makes the nose plug easy to place within both nostrils at the same time and easy to remove. This extension also hinders the nose plug to be placed to deep into a nostril, which could damage soft tissue.

The releasable substance carried by the nose plug may be a fragrance. This is an advantage, since it efficiently hinders the bad odour from reaching the olfactory organs. The releasable substance carried by the nose plug may also be a medicine.

BRIEF DESCRIPTION OF THE DRAWINGS

The present invention will now be described in more detail, and with reference to the accompanying drawings, in which:

FIG. 3 illustrates a cut along A-A in FIG. 2,

FIG. 4 illustrates a cut along B-B in FIG. 2,

DETAILED DESCRIPTION

In the following description, the invention will be described in more detail with reference to certain embodiments and to the accompanying drawings. For purposes of explanation and not limitation, specific details are set forth, such as particular scenarios, techniques, etc., in order to provide a thorough understanding of the present invention. However, it is apparent to one skilled in the art that the present invention may be practised in other embodiments that depart from these specific details.

The expression nose plug used in this application is not a stopper in the sense to close the nostrils completely. While it fills the nostril, thereby hindering air from flowing freely into the nose, it is not intended to entirely hinder air from entering.

Figure 1:
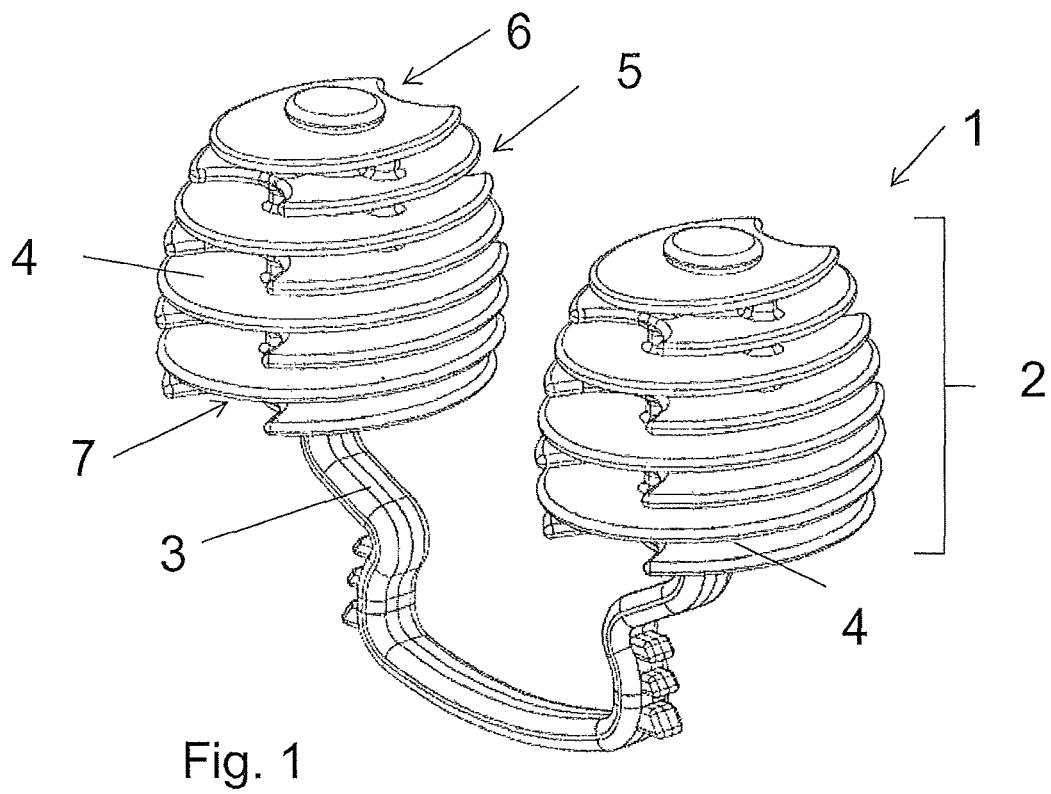
FIG. 1 shows an embodiment of a nose plug in a perspective view.

FIG. 1 shows a nose plug 1 comprising a flexible member 2 and one rigid, elongated support member 3 adapted to stabilize the flexible member. In this embodiment of the nose plug the flexible member 2 comprises parallel plates 4 surrounding the support member. Between adjacent plates there are spaces 5. Furthermore, there is provided for communication between theses spaces through the plates. When the nose plug is placed in a nose and the flexible plates accurately fill the openings of the nostrils, air entering the nostrils will, when passing through the nose plug, first enter through a recess 7 in a first lowermost plate. The air flow then passes the nose plug in a tortuous manner and exits through a recess 6 in an uppermost final plate. This embodiment illustrates a much extended path for the air to flow through, since every second recess is on a position at the periphery that is opposite on the transverse diameter in relation to the recess on an adjacent plate. The recess 7 of the first plate and the recess 6 of the final plate and all the recesses there between are clearly seen in FIG. 4, i.e. the recess 7 of the first lowermost plate and the recess of every second plate counted from the first plate has the same reference number and the recess 6 of the uppermost final plate and every second plate counted from the final plate has the same reference number. This is valid when the number of plates is an even number (as shown in the embodiments in FIGS. 1 to 6), otherwise in the case were the number of the plates is uneven the recess of the first and the final plate will have the same reference number.

In the embodiments of the invention seen in FIGS. 1 to 6 the flexible member 2 is adapted to guide the flow of air entering the nostril in a serpentine or meandering like path. This is achieved when the nose plug is placed in a nostril. The air flow enters the flexible member 2 of the nose plug 1 through the recess 7 of the lowermost plate 4, the air flow is then passing in the space 5 between two adjacent plates, i.e. the first and second plate, arriving at the opposite transverse diametrical end of the first plate, where the air flow is further guided through the recess 6 of the second plate. Thereafter the air flow is passing between two further adjacent plates, i.e. the second and third plate, arriving at the opposite transverse diametrical end of the second plate, where the air flow is further guided through the recess 7 of the third plate. And so on, until the air flow passes between the two uppermost plates and exits into the nostril through the recess 6 of the final plate.

In the embodiment illustrated in FIGS. 1 to 6 the number of the plates is 8. The number of the plates may also be another number such as 6, 7, 9 or 10. The number of the plates is preferably ranging from 4 to 12.

Figure 2:
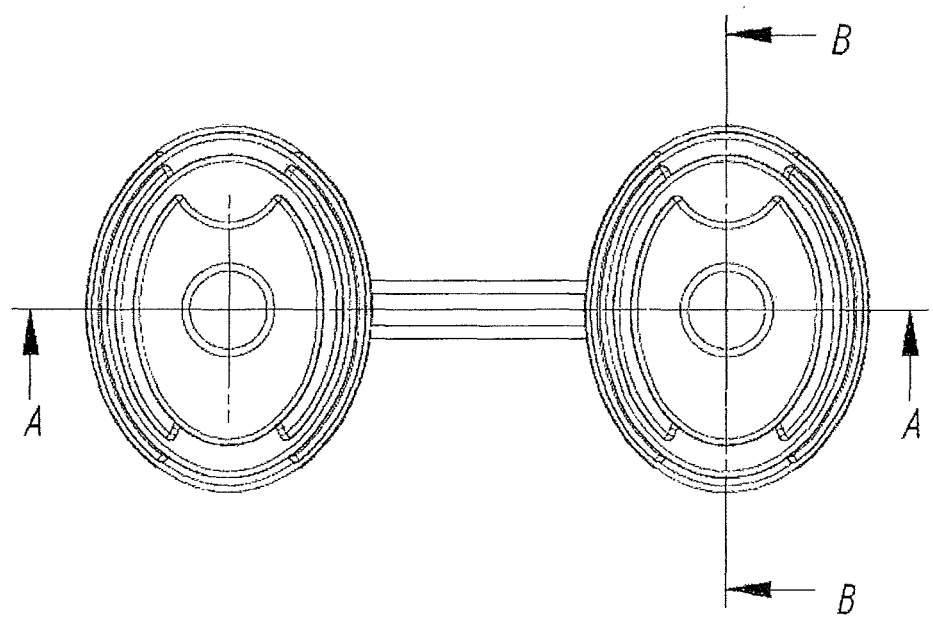
FIG. 2 illustrates the nose plug in FIG. 1 from above.

FIG. 2 shows the nose plug of the embodiment in FIG. 1 from above. As may be seen the plates 4 have an elliptical shape. The final uppermost plate is the smallest (transverse diameter and conjugate diameter) and the plates in the middle, i.e. plate number four and/or five is/are the largest plate(s). The first plate is somewhat larger than the final plate. Seen from the first plate each further adjacent plate has somewhat larger diameters, until the fourth or fifth plate, thereafter each further adjacent plate has somewhat smaller diameters, i.e. from the first to the fourth or fifth plate the transverse and conjugate diameter increases for each plate, from the fourth or fifth plate to the final plate the transverse and conjugate diameter diminishes for each plate. The increase or the diminution of each adjacent plate may be linear, but may also progress irregularly.

In FIG. 2 are the lines A-A and B-B shown. The line A-A coincides with the conjugate diameter of the plates and line B-B coincides with the transverse diameter of the plates.

The flexible member 2 is preferably made of a thermoplastic elastomer. Other flexible materials may also be used. The support member is preferably made of a thermoplastic polymer. Other firm or rigid materials are also possible to use.

In FIG. 3 can the cut along A-A be seen. In this figure the flexible member 2 surrounds the support member 3. The support member 3 has a generally U-shaped form and has two flexible members 2 attached thereto, one on each leg. The support member 3 extending between the two flexible members 2 has a bent shape, in order to be easy to handle.

In FIG. 4 is the cut along B-B shown. This cut coincides with the transverse diameters of the plates 4. Therefore, the recesses 6 of every second plate are shown on the one side and the recesses 7 of every other second plate are shown on the other side.

Figure 5:
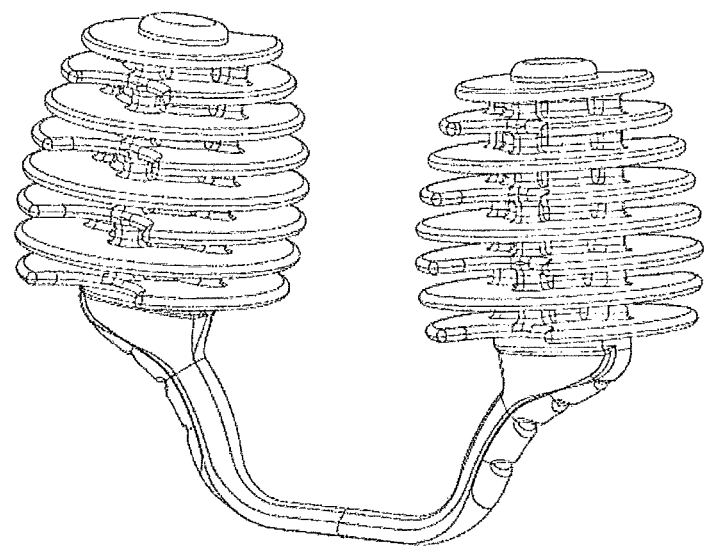
FIG. 5 shows a nose plug moulded by using a 2K technique.

As can be seen in FIG. 5 the two legs of the generally U-shaped support member 3 are slightly inclined towards each other. This is due to adapting the nose plug to the extension of the nostrils. The plug shall be properly arranged within the nose, without widening the nostrils more than necessary.

The releasable substance dispersed in the flexible material or arranged on the surface of the flexible member 2 may be a fragrance, medicine, nicotine or any other releasable substance. The nose plug may also be used as a filter that hinders particles from entering the nose and be further dispersed in other organs. When used as a filter the surface of the flexible material may be treated by an appropriate process in order to efficiently hinder particles from being further dispersed.

The nose plug according to the invention may be manufactured by moulding using a 2K technique, where two materials are moulded together. This may e.g. be seen in FIGS. 5 to 7. The method of manufacturing the nose plug may also comprise other techniques. For instance, only one material may be used for manufacturing the entire nose plug, i.e. the same material for the flexible member as for the support member. Furthermore, the flexible member and the support member comprised in the nose plug according to the invention may also be manufactured by moulding them separately.

Figure 6:
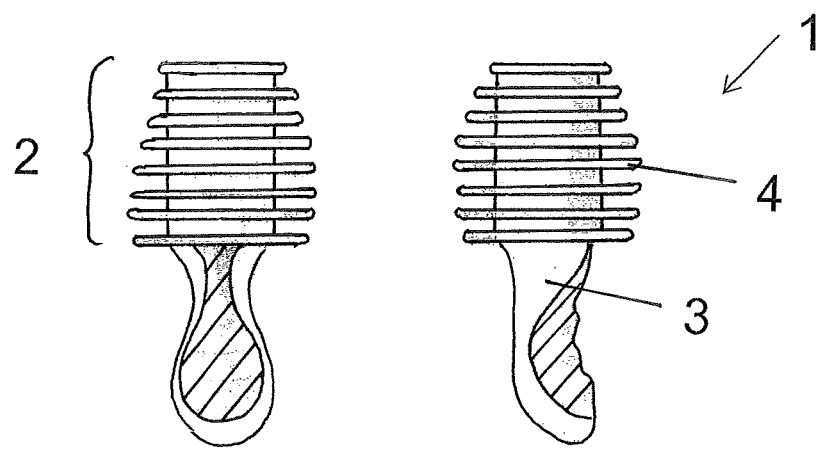
FIG. 6 illustrates an embodiment of a nose plug.

FIG. 6 illustrates an embodiment of the invention, wherein each nose plug, comprises one flexible member arranged on a support member, is adapted to be arranged separately in one nostril each.

Figure 7:
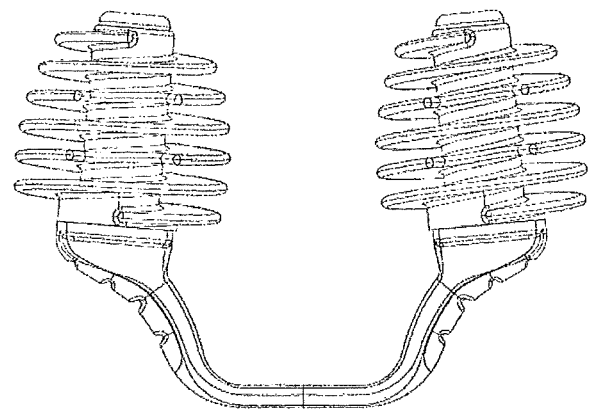
FIG. 7 shows a helical embodiment of a nose plug in a perspective view.

FIG. 7 shows an embodiment with a flexible member comprising a helically arranged band in a perspective view. This spiral like structure gives the air entering the nostrils an extended path. The distance of the path may be varied due to the pitch angle of the helical wings of the band. There may also be recesses provided on the helically arranged band. But since air is allowed to enter without recesses, this is not an essential feature.

Figure 8:
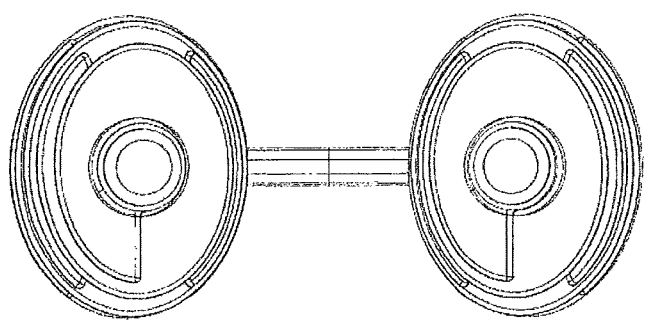
FIG. 8 shows a helical embodiment of a nose plug from above.

In FIG. 8 the embodiment in FIG. 7 is seen from above. The helically arranged band shown in FIGS. 7 and 8 shows the flexible member being adapted to guide the flow of air entering the nostril in a spiral like path.

Further, the above mentioned and described embodiments are only given as examples and should not be limited to the present invention. Other solutions, uses, objectives, and functions within the scope of the invention as claimed in the accompanying patent claims should be apparent for the person skilled in the art.

The invention claimed is:

1. A nose plug (1) comprising:
a rigid, elongated support member (3); and
a flexible member (2) adapted to be placed within a nostril to accurately fill an opening of the nostril, wherein the flexible member (2) comprises
i) parallel plates (4) surrounding the rigid, elongated support member (3) and defining an extended serpentine air path and wherein the parallel plates (4) are adapted to guide air entering the nostril along the extended serpentine air path,
wherein the flexible member (2) comprises four to twelve of said parallel plates (4), the parallel plates (4) arranged along the rigid, elongated support member (3) and where each of the parallel plates (4) extends in a direction perpendicular to an extension of the rigid, elongated support member (3), and
wherein each of the parallel plates (4) has one recess at a periphery thereof, and each said recess is arranged to not overlap a corresponding said recess in a previous one of the parallel plates (4) or a subsequent one of the parallel plates (4), and each parallel plate (4) is adapted to guide the air entering the nostril from a lower side of each parallel plate (4) to an upper side of each parallel plate (4) by each said one recess providing an air pathway across each corresponding parallel plate (4).

2. The nose plug (1) according to claim 1, wherein the nose plug (1) carries a releasable substance dispersed in a material of the flexible member (2) or arranged on a surface of the flexible member (2).

3. The nose plug (1) according to claim 2, wherein the releasable substance is a fragrance.

4. The nose plug (1) according to claim 2, wherein the releasable substance is a medicine.

5. The nose plug (1) according to claim 1, wherein the parallel plates (4) have a rounded shape.

6. The nose plug (1) according to claim 5, wherein the parallel plates (4) have differently sized peripheries, in order to adapt the nose plug (1) to a shape of an inside of a nostril.

7. The nose plug (1) according to claim 5, wherein a first set of said recesses is arranged on every second one of the parallel plates (4) at a position at a periphery of a first end of a transverse diameter and a second set of said recesses are arranged on every parallel plate there between at a periphery at an opposite, second end of the transverse diameter.

8. The nose plug (1) according to claim 1, wherein the flexible member (2) defines a filter adapted to hinder particles from entering the nostril and being dispersed in other organs.

9. The nose plug (1) according to claim 8, wherein a surface of the flexible member (2) is adapted to efficiently hinder particles from being further dispersed.

10. The nose plug (1) according to claim 1, wherein the parallel plates (4) have differently sized peripheries, in order to adapt the nose plug (1) to a shape of an inside of a nostril.

11. The nose plug (1) according to claim 1, wherein a first set of said recesses is arranged on every second one of the parallel plates (4) on a position at a periphery at a first end of a transverse diameter and a second set of said recesses are arranged on every parallel plate there between at a periphery at an opposite, second end of the transverse diameter.

12. The nose plug (1) according to claim 1, wherein the flexible member (2) and the rigid, elongated support member (3) are permanently fixed to each other.

13. The nose plug (1) according to claim 1 further comprising two of said flexible member (2) connected to each other by a U-shaped support member, each of said two flexible members (2) being attached at one leg of said U-shaped support member.

* * * * *